(12) United States Patent
Alcon-Marrugat et al.

(10) Patent No.: US 6,958,403 B2
(45) Date of Patent: Oct. 25, 2005

(54) PROCEDURE FOR THE PREPARATION OF RACEMIC AND ENANTIOMERICALLY PURE DERIVATIVES OF 1,5 DIARYL-3-TRIFLUORROMETHYL-$\Delta^2$-PYRAZOLINES

(75) Inventors: Montserrat Alcon-Marrugat, Barcelona (ES); Miguel Angel Pericas-Brondo, Barcelona (ES); Maria Rosa Cuberes-Altisen, Barcelona (ES); Jordi Frigola-Constansa, Barcelona (ES)

(73) Assignee: Laboratorios del Dr. Esteve, S.A., (ES)

( * ) Notice: Subject to any disclaimer, the term of this patent is extended or adjusted under 35 U.S.C. 154(b) by 0 days.

(21) Appl. No.: 11/007,449

(22) Filed: Dec. 8, 2004

(65) Prior Publication Data

US 2005/0096373 A1    May 5, 2005

Related U.S. Application Data

(62) Division of application No. 10/312,194, filed as application No. PCT/ES02/00274 on Jun. 6, 2002, now Pat. No. 6,846,935.

(30) Foreign Application Priority Data

Jun. 18, 2001   (ES) .................................. 200101412

(51) Int. Cl.$^7$ .......................................... C07D 231/06
(52) U.S. Cl. .................................. 548/379.4; 548/379.7
(58) Field of Search ........................... 548/379.4, 379.7

(56) References Cited

U.S. PATENT DOCUMENTS 3,865,816 A * 2/1975 Mengler .................. 548/379.7

FOREIGN PATENT DOCUMENTS

WO    WO 99/62884    12/1999
WO    WO 00/76503    12/2000

OTHER PUBLICATIONS

M. Mukai, et al. "On the Syntheses and the Optical Properties of Optically Active 2-Pyrazoline Compounds", *Canadian J. of Chemistry* (1979), 57(3), pp. 360.
J. Jacques, et al. "Enantiomers, Racemates and Resolutions", 1991, *Krieger Publishing Company*, Florida, U.S.A, pp. 258-259.
Leonardo et al., *Chirality* (2004), 16(6), pp. 302-308 (CAS Abstract).

* cited by examiner

Primary Examiner—Kamal A. Saeed
(74) Attorney, Agent, or Firm—Ostrolenk, Faber, Gerb & Soffen, LLP

(57) ABSTRACT

Procedure for preparation of compounds with the general formula 1, which include the racemic mixtures ($\pm$)-1, and the enantiomerically pure compounds ($-$)-1 and (+)-1, wherein $R_1$ and $R_3$, like or different, represent an atom of hydrogen, chlorine, fluorine, a methyl, trifluoromethyl or methoxy group; $R_2$ represents an atom of hydrogen, chlorine, fluorine, a methyl, trifluoromethyl, methoxy, trifluoromethoxy, methylsulphonyl or aminosulphonyl group; $R_4$ represents an atom of hydrogen, chlorine, fluorine, a methyl, trifluoromethyl, methoxy, trifluoromethoxy, methylsulphonyl or aminosulphonyl group, with the condition that one of the substituents $R_2$ or $R_4$ is a methylsulphonyl or aminosulphonyl group; which involves obtaining the racemic mixture with the general formula ($\pm$)-1 by reacting an (E)-1,1,1-trifluoro-4-aryl-3-buten-2-one with a phenylhydrazine, followed by a treatment with chlorosulphonic acid, or by reacting with chlorosulphonic acid followed by a reaction with sodium hydroxide and, finally, with thionyl chloride. The product obtained by either of these methods is made to react with ammonium carbonate or ammonia, or with sodium sulphite and methyl iodide or methyl sulphate. In addition, to obtain the enantiomerically pure compounds with the general formula 1 by resolving the racemic mixture with the general formula ($\pm$)-1, a reaction is effected with optically active ephedrine, followed by formation of the sodium salt of each enantiomer, reaction with thionyl chloride and ammonium carbonate or ammonia, or instead with thionyl chloride followed by sodium sulphite and methyl iodide or methyl sulphate to thereby obtain separately the enantiomerically pure compounds with the general formulae ($-$)-1 and ($\pm$)-1.

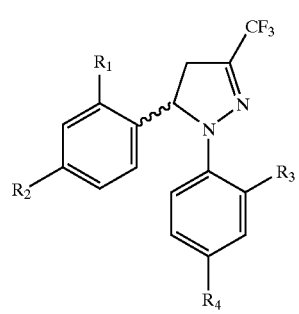

1 Claim, No Drawings

PROCEDURE FOR THE PREPARATION OF RACEMIC AND ENANTIOMERICALLY PURE DERIVATIVES OF 1,5 DIARYL-3-TRIFLUORROMETHYL-$\Delta^2$-PYRAZOLINES

CROSS REFERENCE TO RELATED APPLICATIONS

This application is a divisional of application Ser. No. 10/312,194, filed Dec. 17, 2002, now U.S. Pat. No. 6,846,935, which is a 371 of International Application No. PCT/ES02/00274, filed Jun. 6, 2002.

FIELD OF THE INVENTION

The present invention relates to a new, commercially useful procedure for the preparation of compounds having the general formula 1, which includes the racemic mixture (±)—1, and the enantiomerically pure compounds (−)-1 and (+)-1.

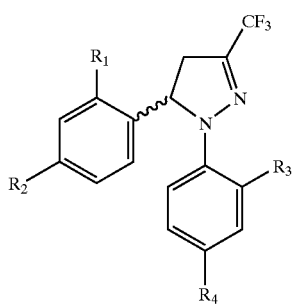

1

BACKGROUND OF THE INVENTION

Our Patent WO 9962884 describes new derivatives of $\Delta^2$-pyrazolines, also known as 4,5-dihydro-1H-pyrazoles, which inhibit the enzyme cyclooxygenase-2, with application in human and/or veterinary medicine as anti-inflammatories and in other diseases in which cyclooxygenase-2 is involved, and which present a low or zero gastric and renal toxicity, so that they are anti-inflammatories with a greater safety profile. Certain racemic mixtures (±)—1, and the enantiomerically pure stereoisomers (−)-1 and (+)-1 described in said Patent are currently in a clinical investigation stage. The aforementioned Patent describes the preparation of (±)-1 by reaction of (E)-1,1,1-trifluoro-4-aryl-3-buten-2-one with 4-(aminosulphonyl)phenylhydrazine or 4-(methylsulphonyl)phenylhydrazine, or by reaction of 4-(aryl)phenylhydrazine with (E)-1,1,1-trifluoro-4-(4-aminosulphonylphenyl)-3-buten-2-one or (E)-1, 1,1-trifluoro-4-(4-methylsulphonylphenyl)-3-buten-2-one. It also describes the production of (−)-1 and (+)-1 by resolution of the racemic mixture (±)-1 using high resolution liquid chromatography with a CHIRALPAK AS column of de $10\mu$ particle size and dimensions 25×2 cm (Daicel), mobile phase 0.1% of diethylamine in methanol and flow rate of 8 ml/min.

In addition, the methods for resolution of racemic mixtures described in the literature are numerous and have been widely used [a] for a monograph of the properties of racemates and their resolutions see Jacques, Collet, Wilen "Enantiomers Racemates and Resolutions", Wiley: New York, 1981; for reviews see: b) Wilen, Top. Stereochem., 1971, 6, 107; c) Boyle, Q. Rev. Chem. Soc., 1971, 25; d) Buss, Vermeulen, Ind. Eng. Chem., 1968, 60, 12]. However, there are few examples in the scientific literature regarding resolution of $\Delta^2$_pyrazolines [Toda, J. Chem. Soc., Chem. Commun., 1995, 1453]. This paper describes the resolution of a $\Delta^2$-pyrazoline by formation of an inclusion complex. A prior paper [Mukai, Can. J. Chem., 1979, 57, 360–366] develops the resolution of an optically active assembly of $\Delta^2$-pyrazolines-sodium benzenosulphate from the corresponding racemics, using as resolution agents cinconidine, (−)-$\alpha$-methylbenzylamine and brucine, depending on the substrate. This method has the disadvantage of using successive recrystallisations in both the process of formation of sodium sulphonate (between 3 and 7 recrystallisations), and in the process of formation and separation of the mixture of diastereoisomeric salts (between 4 and 7 recrystallisations), which results in a considerable reduction of the yield.

We have now found a strategy for preparing compounds with the general formula 1 which consists of using derivatives of benzaldehyde much cheaper than 4-(aminosulphonyl)benzaldehyde or 4-(methylsulphonyl)benzaldehyde for obtaining (E)-1,1,1-trifluoro-4-aryl-3-buten-2-one, and derivatives of phenylhydrazine much cheaper than 4-(aminosulphonyl)phenylhydrazine or 4-(methylsulphonyl)phenylhydrazine. The enone and hydrazine are used to obtain the ring of $\Delta^2$-pyrazoline, which process when sequentially combined with a sulphonation and an optical resolution process to obtain the enantiomerically pure compounds of the racemic sulphonic acid using an optically active base, or a mixture of bases in which at least one is optically active, leads to the formation of diastereoisomeric salts. The process continues with the separation of these salts, transformation into the sodium salt, formation of the acid chloride and obtaining the enantiomerically pure sulphonamide or sulphone 1.

The present invention provides a method of preparing the racemic mixture of the compound with formula (±)-1,

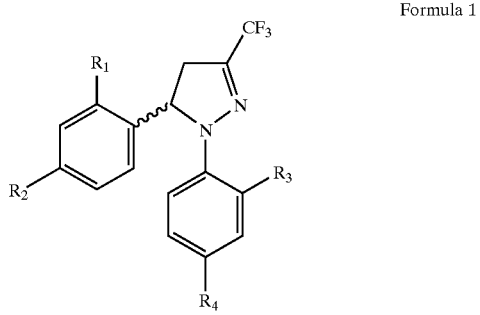

Formula 1 wherein
each of $R_1$ and $R_3$ which may be the same or different is selected from the group consisting of hydrogen, chlorine, fluorine, methyl, trifluoromethyl and methoxy; and each of $R_2$ and $R_4$ which may be the same or different is selected from the group consisting of hydrogen, chlorine, fluorine, methyl, trifluoromethyl, methoxy, trifluoromethoxy, methylsulphonyl and aminosulphonyl;

with the condition that one of the substituents $R_2$ or $R_4$ is a methylsulphonyl or aminosulphonyl group;

method comprising preparing the racemic mixture with the general formula (±)-1 by:

(a) reacting an (E)-1,1,1-trifluoro-4-aryl-3-buten-2-one (formula 2) with a phenylhydrazine (formula 3),

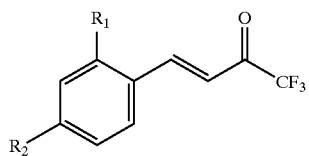

Formula 2

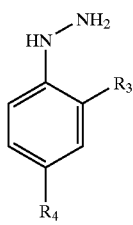

Formula 3 wherein each of $R_1$ and $R_3$, which may be the same or different is selected from the group consisting of hydrogen, chlorine, fluorine, methyl, trifluoromethyl and methoxy;

and each of $R_2$ and $R_4$ which may be the same or different is selected from the group consisting of hydrogen, chlorine, fluorine, a methyl, trifluoromethyl, methoxy and trifluoromethoxy group;

with the condition that at least one of the substituents $R_2$ or $R_4$ is a hydrogen;

in order to obtain a pyrazoline with the general formula (±)-4,

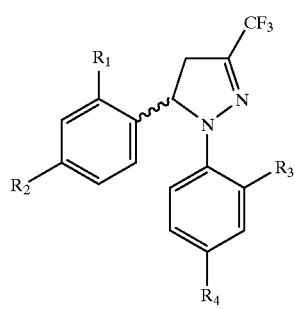

Formula 4 wherein each of $R_1$ and $R_3$ which may be the same or different is selected from the group consisting of hydrogen, chlorine, fluorine, methyl, trifluoromethyl and methoxy; and each of $R_2$ and $R_4$ which may be the same or different is selected from the group consisting of hydrogen, chlorine, fluorine, methyl, trifluoromethyl, methoxy and trifluoromethoxy;

with the condition that at least one of the substituents $R_2$ or $R_4$ is a hydrogen;

(b) reacting the compound of formula (±)-4 with chlorosulphonic acid to form a pyrazoline with the formula (±)-5,

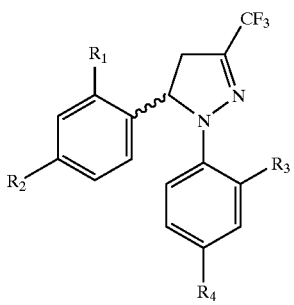

Formula 5 wherein each of $R_1$ and $R_3$ which may be the same or different is selected from the group consisting of hydrogen, chlorine, fluorine, methyl, trifluoromethyl and methoxy; and each of $R_2$ and $R_4$ which may be the same or different is selected from the group consisting of hydrogen, chlorine, fluorine, methyl, trifluoromethyl, methoxy, trifluoromethoxy and sulphonyl chloride, with the condition that one of the substituents $R_2$ or $R_4$ is a sulphonyl chloride group ($SO_2Cl$);

or alternatively reacting the compound of formula (±)-4 with chlorosulphonic acid followed by reaction with sodium hydroxide to form the pyrazoline with the formula (±)-6,

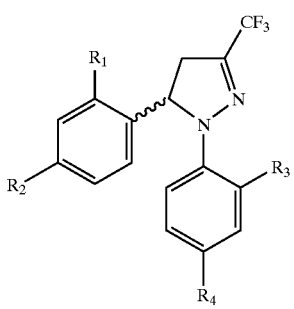

Formula 6 wherein each of $R_1$ and $R_3$, which may be the same or different is selected from the group consisting of hydrogen, chlorine, fluorine, methyl, trifluoromethyl and methoxy group, and each of $R_2$ and $R_4$ which may be the same or different is selected from the group consisting of hydrogen, chlorine, fluorine, methyl, trifluoromethyl, methoxy, trifluoromethoxy and sodium sulphonate group, with the condition that one of the substituents $R_2$ or $R_4$ represents a sodium sulphonate group ($SO_3Na$);

(c) reacting the pyrazoline of either the formula (±)-5 or the formula (±)-6 with thionyl chloride to form the pyrazoline with the formula (±)-7,

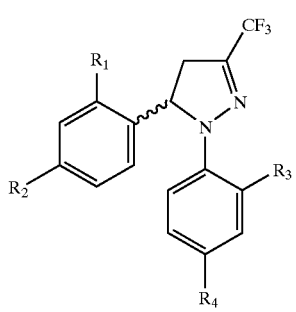

Formula 7 wherein each of $R_1$ and $R_3$, which may be the same or different is selected from the group consisting of hydrogen, chlorine, fluorine, a methyl, trifluoromethyl and methoxy; and each of $R_2$ and $R_4$ which may be the same or different is selected from the group consisting of hydrogen, chlorine, fluorine, methyl, trifluoromethyl, methoxy, trifluoromethoxy and sulphonyl chloride, with the condition that one of the substituents $R_2$ or $R_4$ represents a sulphonyl chloride group ($SO_2Cl$); and (d) reacting the pyrazoline with the formula (±)-7 with one compound selected from the group consisting of ammonium carbonate, ammonia, sodium sulphite combined with methyl iodide and methyl sulphate resulting in the racemic mixture of the compound with formula (±)-1.

DETAILED DESCRIPTION OF THE INVENTION

The object of the present invention consists of providing a commercially useful procedure for preparing compounds with the general formula 1, which includes the racemic mixture (±)-1 and the enantiomerically pure compounds (−)-1 and (+)-1, where $R_1$ and $R_3$, identical or different, represent an atom of hydrogen, chlorine, fluorine, a methyl, trifluoromethyl or methoxy group, $R_2$ represents an atom of hydrogen, chlorine, fluorine, a methyl, trifluoromethyl, methoxy, trifluoromethoxy, methylsulphonyl or aminosulphonyl group, $R_4$ represents an atom of hydrogen, chlorine, fluorine, a methyl, trifluoromethyl, methoxy, trifluoromethoxy, methylsulphonyl or aminosulphonyl group, With the condition that one of the substituents $R_2$ or $R_4$ is a methylsulphonyl or aminosulphonyl group.

The present invention discloses a method for obtaining the racemic mixture (±)-1 that is less expensive than the one described previously in Patent WO 9962884 as it uses phenylhydrazine instead of 4-(aminosulphonyl)phenylhydrazine or 4-(methylsulphonyl)phenylhydrazine, or benzaldehyde instead of 4-(aminosulphonyl)benzaldehyde or 4-(methylsulphonyl)benzaldehyde to obtain the ring of $\Delta^2$-pyrazoline, represented in the scheme 1 as the compound (±)-2. By means of sulphonation the acid chloride is obtained, which is made to react with ammonia or ammonium carbonate to obtain the sulphonamide ($R_2$ or $R_4=SO_2NH_2$), or with sodium sulphite and the sodium sulphinate obtained with methyl sulphate or methyl iodide to obtain the methylsulphone ($R_2$ or $R_4=SO_3CH_3$), (±)-1. It is also possible to isolate the corresponding sodium salt: by sulphonation and treatment with sodium hydroxide the salt (±)-3 is obtained, which is reacted with thionyl chloride and the acid chloride obtained is reacted with ammonia or ammonium carbonate to obtain the sulphonamide ($R_2$ or $R_4=SO_2NH_2$), or instead with sodium sulphite and the sodium sulphinate obtained with methyl sulphate or methyl iodide to obtain the methylsulphone ($R_2$ or $R_4=SO_2CH_3$), (±)-1.

It also provides an industrial application method for obtaining the enantiomerically pure stereoisomers (+)-1 and (−)-1. One pair of enantiomers can be resolved by various methods, with conversion to diastereoisomeric salts and their separation by fractioned crystallisation being the most commonly used. Once the diastereoiseomeric salts have been obtained and separated the enantiomers (acids or bases) can be easily liberated, and the chiral acid or base recovered, so that this simple and inexpensive method has been widely used for industrial applications. If the racemic compound contains an amine group in its structure it is possible to form diastereoisomeric salts with an optically active acid, and it the racemic compound contains an acid group it is possible to form diastereoisomeric salts with an optically active base. Since the compound 1 lacks any acid or basic groups strong enough to form diastereoisomeric salts the present invention develops a procedure which is described schematically below (Schematic 1) for obtaining the racemic mixture (±)-1 and the enantiomerically pure compounds (−)-1 and (+)-1.

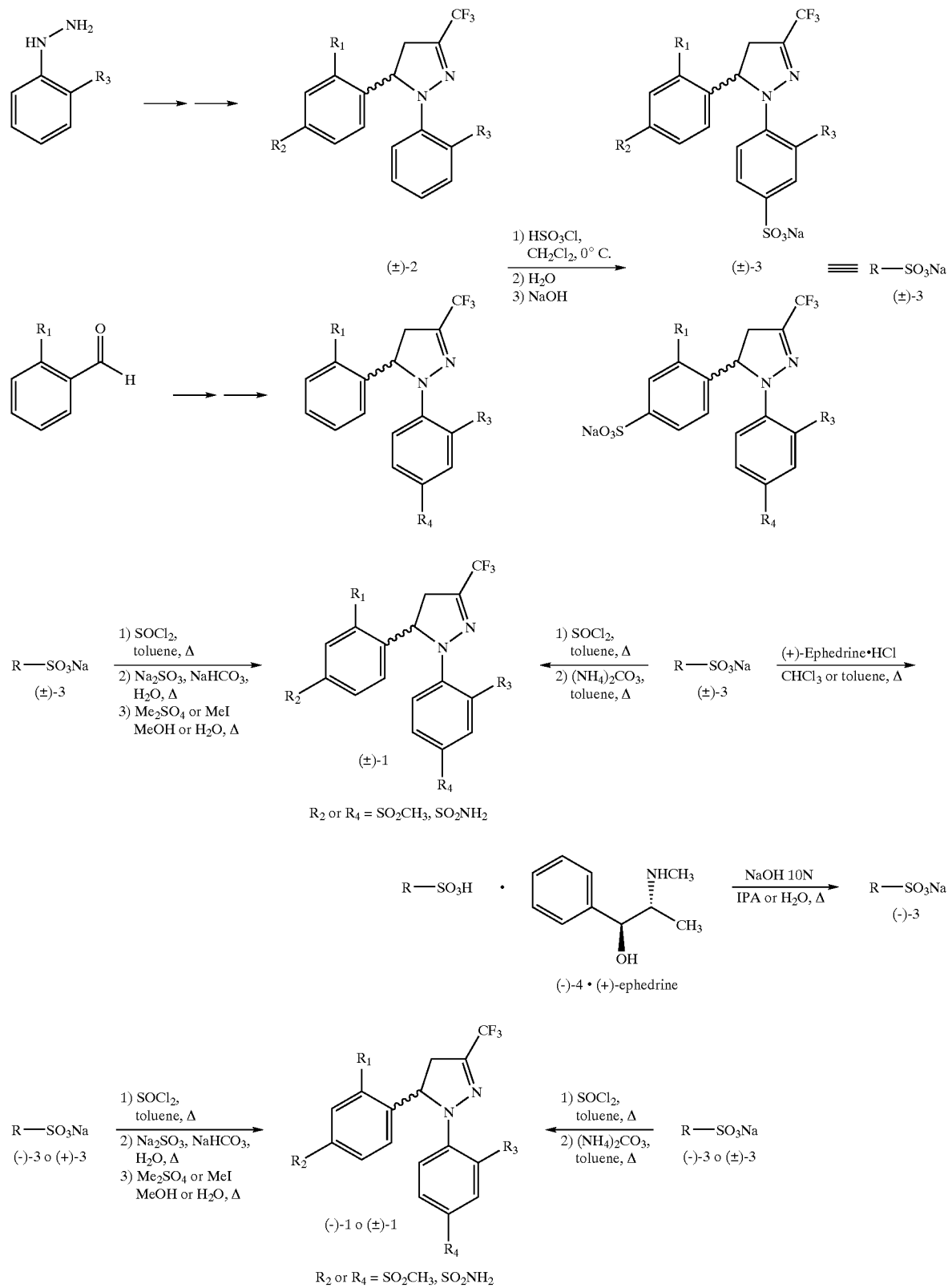

The procedure developed in the present invention is described schematically below for two specific examples: firstly (Schematic 2) for obtaining the enantiomerically pure compound (−)-8.

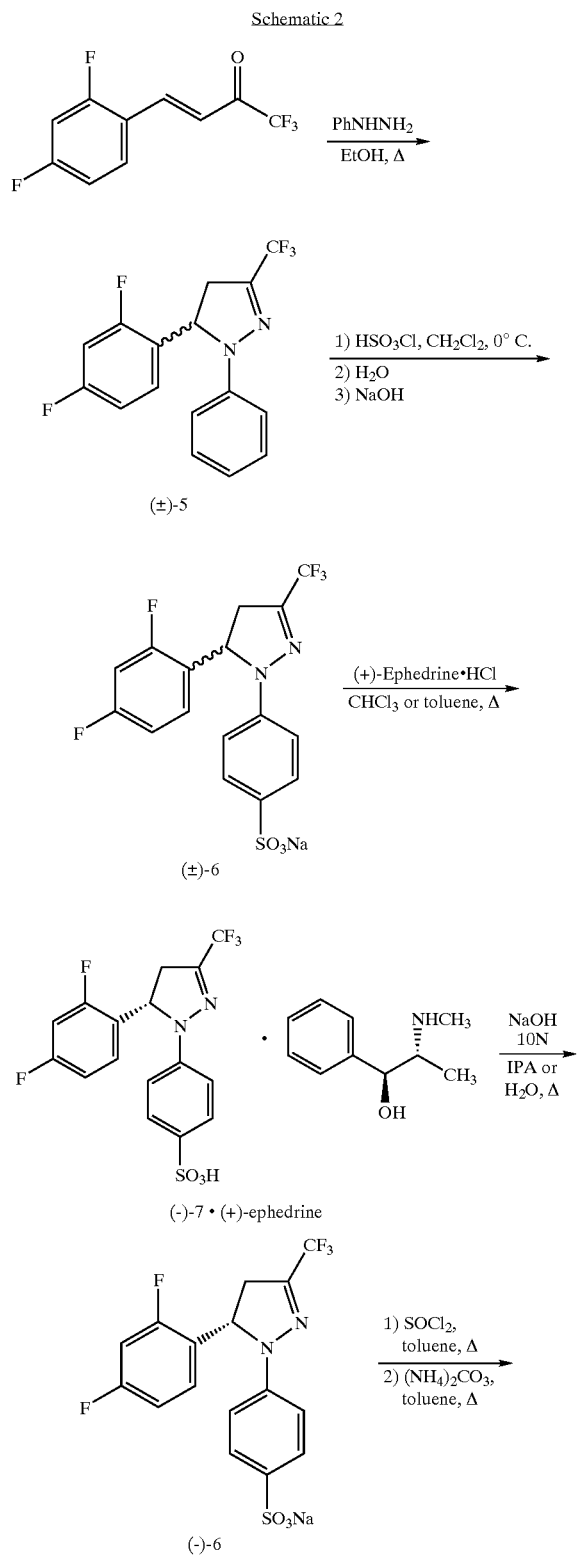

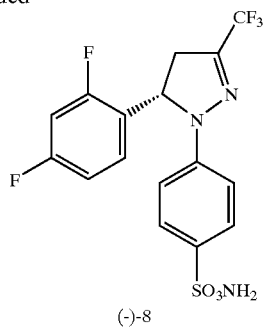

(−)-8

The compound (−)-8 is synthesised, in accordance with the present invention, by the method described below with the schematic indicating certain preferred conditions. The third stage involves the resolution of the racemic mixture (±)-6 into its two enantiomers, using as a resolution agent (+)-ephedrine. Ephedrine is an excellent resolving agent; as both enantiomers can be used in the resolution, they are available in a high enantiomeric concentration, are commercially available and are easily recoverable and crystallisable. The compound (+)-8 is prepared by the same synthesis path as in the previous case, changing only the ephedrine enantiomer in the resolution process (step 3). Synthesis of the racemic compound (±)-8 is performed in the same manner, skipping the steps related to resolution, that is, directly by reaction of the acid chloride with ammonium or ammonium carbonate.

The first stage consists of preparing the pyrazoline (±)-5 from (E)-1,1,1-trifluoro-4-(2,4-difluorophenyl)-3-buten-2-one and phenylhydrazine, in a suitable solvent, for example in alcohols such as methanol, ethanol or isopropanol, or in the absence of a solvent. The reaction takes place in an acid medium, which can be organic such as acetic acid or p-toluensulphonic acid, or inorganic such as hydrochloric acid, or a mixture of both, or instead in an alkali medium such as in piperidine, piperazine, sodium hydroxide, potassium hydroxide, sodium methoxide or sodium ethoxide, or a mixture thereof. The same acid or alkali medium can also act as a solvent. The most suitable temperatures range from ambient temperature to 150° C., and reaction times lie between 2 and 48 hours. Purification of pyrazoline (±)-5 is carried out by crystallisation.

In the second step a sulphonation is performed on the pyrazoline (±)-5 with chlorosulphonic acid without a solvent or using a chlorinated solvent such as dichloromethane at temperatures ranging between 0° C. and the boiling temperature of the solvent, providing the corresponding sulphonic acid after an aqueous treatment. Addition of sodium hydroxide precipitates the sodium sulphonate (±)-6.

In the third step the racemic mixture (±)-6 is resolved into its two enantiomers by forming a mixture of two diastereoisomeric salts and the subsequent separation of one of these by precipitation in the same reaction medium. The procedure object of the present invention does not suffer from the aforementioned drawbacks in resolution of a similar product as performed by Mukai et al. [Can. J. Chem. 1979 57, 360–366], and separation of the two diastereoisomeric salts is performed in the same reaction medium during the process of forming the mixture of diastereoisomeric salts, that is, a single crystallisation is required. The resolution agent employed is (+)-ephedrine, which by reaction of the racemic mixture (±)-6 with (+)-ephedrine chlorhydrate in a chlorinated solvent such as chloroform and at temperatures oscillating ranging from ambient temperature and the reflux temperature provides the mixture of diastereoisomeric salts, and in the cooling process only the enantiomer (−)-7 precipitates in the form of a salt of (+)-ephedrine, with an enantiomeric excess above 98%. It is possible to obtain from the filtration liquids the diatereoisomeric salt of (+)-7 and (+)-ephedrine, by evaporation of the solvent and subsequent recrystallisation in an alcohol, such as isopropyl alcohol, or mixtures of an alcohol and water. In addition, by the same process of step 3 of the schematic but using (−)-ephedrine chlorhydrate, the diastereoisomeric salt formed by (+)-7 and (−)-ephedrine is obtained by precipitation and from the filtration liquids can be obtained the diatereoisomeric salt of (−)-7 and (−)-ephedrine, by evaporation of the solvent and subsequent recrystallisation in an alcohol, such as isopropyl alcohol, or mixtures of an alcohol and water.

In the fourth stage shown in the reaction scheme the sodium sulphonate (−)-6 is released in enantiomerically pure form by basic hydrolysis of the salt (−)-7·(+)-ephedrine, with aqueous sodium hydroxide and using and alcohol such as isopropanol as solvent. From the filtration liquids it is simple to recover the ephedrine by eliminating the solvent and acidifying the residue dissolved in ethanol with ethanolic hydrochloric acid. The enantiomer (+)-6 is obtained in the same manners from the salt (+)-7·(+)-ephedrine or (+)-7·(−)-ephedrine.

The fifth and last step shown in the schematic involves preparation of the stereoisomer (−)-8 with an enantiomeric excess above 98% by reaction of the optically active sodium sulphonate (−)-6 with thionyl chloride in the absence of a solvent or in a suitable solvent such as toluene, at temperatures between ambient temperature and the reflux temperature, and subsequent formation of the sulphonamide adding ammonia or ammonium carbonate to the reaction medium. In the same manner the enantiomer (+)-8 can be obtained from (+)-6. Eliminating the steps related to resolution it is possible to obtain the racemic compound (±)-8.

Scheme 3 shows another specific example for obtaining the compounds object of the invention: preparation of (−)-13.

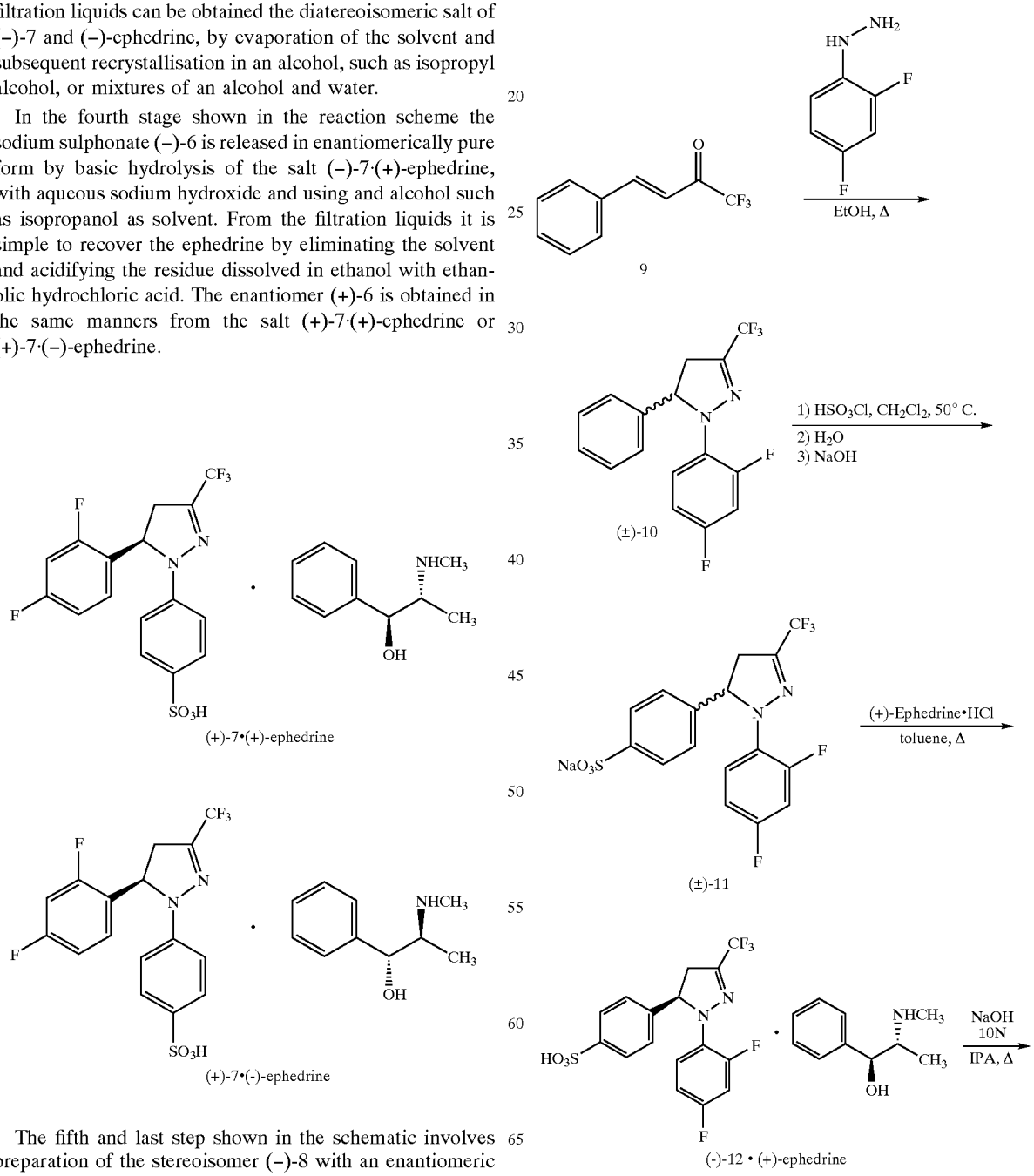

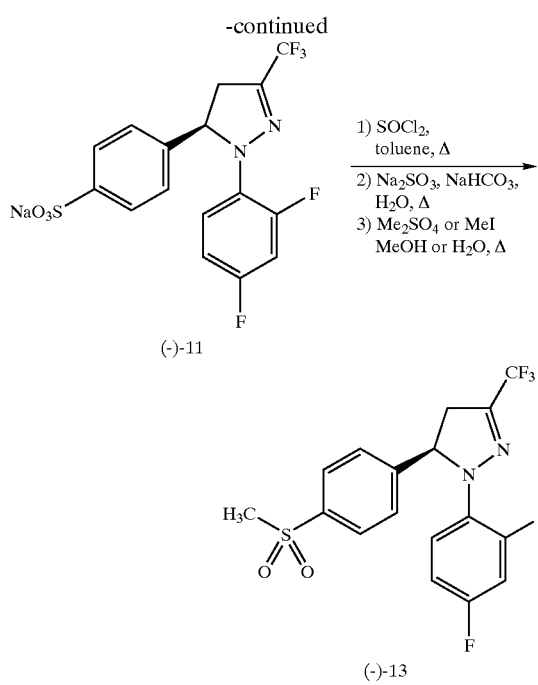

(-)-11

1) SOCl₂, toluene, Δ
2) Na₂SO₃, NaHCO₃, H₂O, Δ
3) Me₂SO₄ or MeI MeOH or H₂O, Δ

(-)-13

The compound (−)-13 is synthesised, according to the present invention, by the method described below, with preferred conditions indicated in the schematic. The third stage involves the resolution of the racemic mixture (±)-11 into its two enantiomers, by formation of a mixture of diastereoisomeric salts, using as a resolving agent (+)-ephedrine to obtain the enantiomer (−)-13. The compound (+)-13 is prepared by the same synthesis path of the previous case, changing only the enantiomer of ephedrine in the resolution process (step 3). Synthesis of the racemic compound (±)-13 is effected in the same way, skipping the formation process for the ephedrine salt and its subsequent hydrolysis.

The first step consists of preparation of pyrazoline (±)-10 from (E)-1,1,1-trifluoro-5-phenyl-3-buten-2-one and 2,4-difluorophenylhydrazine chlorhydrate in a suitable solvent, such as alcohols as ethanol, or in the absence of a solvent. The reaction takes place in an acid medium, such as with acetic acid or p-toluensulphonic acid. The most suitable temperatures lie between ambient temperature and 110° C., and reaction times are between 2 and 24 hours. Purification of the pyrazoline (±)-10 is performed by crystallisation.

In the second step a sulphonation is performed of the pyrazoline (±)-10 with chlorosulphonic acid without a solvent or with a chlorinated solvent such as dichloromethane, at temperatures between 0° C. and the boiling point of the solvent, obtaining the corresponding sulphonic acid after an aqueous treatment. Addition of sodium hydroxide precipitates the sodium sulphonate (±)-11.

In the third step the racemic mixture (±)-11 is resolved into its two enantiomers by forming a mixture of two diastereoisomeric salts and a subsequent separation of one by precipitation in the same reaction medium, with a single crystallisation being required. The mixture of diastereoisomeric salts is prepared by reacting the racemic mixture (±)-11 with (+)-ephedrine chlorhydrate in a suitable solvent such as toluene, at temperatures between ambient temperature and the reflux temperature. In the cooling process only the enantiomer (−)-12 precipitates in the form of a salt of (+)-ephedrine, with an enantiomeric excess of 84%. From the filtration liquids can be obtained the diastereoisomeric salt of (+)-12 and (+)-ephedrine. In addition, by means of the same process of step 3 of the schematic but using (−)-ephedrine chlorhydrate is obtained by precipitation the diastereoisomeric salt formed by (+)-12 and (−)-ephedrine and from the filtration liquids is obtained the diastereoisomeric salt of (−)-12 and (−)-ephedrine.

In the fourth step shown in the reaction schematic the sodium sulphonate (−)-11 is obtained enantiomerically pure by a basic hydrolysis of the salt (−)12·(+)-ephedrine with aqueous sodium hydroxide using water as a solvent. From the filtration liquids it is simple to recover the ephedrine, as described above, by acidifying the residue dissolved in ethanol with ethanolic hydrochloric acid. Preparation of the enantiomer (+)-11 is effected in the same manner from the salt (+)-12·(+)-ephedrine or (+)-12·(−)-ephedrine.

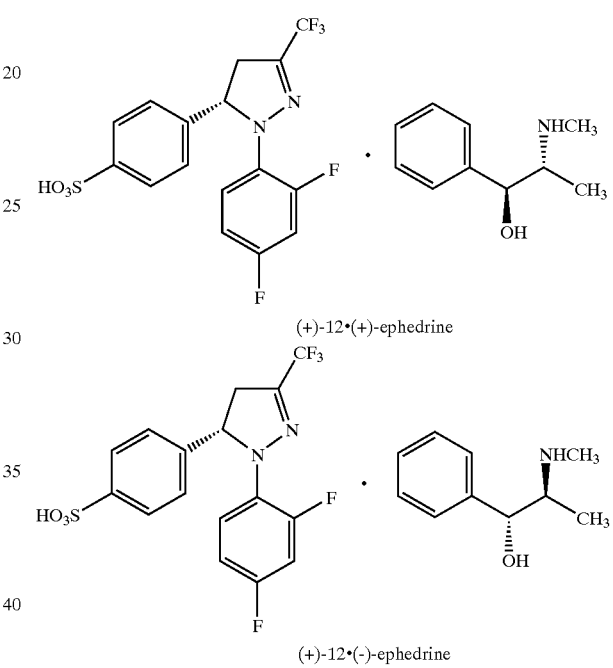

(+)-12•(+)-ephedrine (+)-12•(−)-ephedrine

In the fifth and last step shown the stereoisomer (−)-13 is prepared by reacting the optically active sodium sulphonate (−)-11 with thionyl chloride in the absence of a solvent or in a suitable solvent such as toluene, at temperatures between ambient temperature and the reflux temperature, with subsequent formation of the sodium sulphinate by reaction of the acid chloride with sodium sulphite in a basic aqueous medium, and finally by reaction of the sodium sulphinate obtained with methyl iodide or methyl sulphate in an alcoholic or aqueous medium. In the same manner the enantiomer (+)-13 is obtained from (+)-11. Eliminating the steps related to the resolution the racemic compound (±)13 is obtained.

The resolution process object of the present invention can be used or racemic mixtures (those in which the two enantiomers are present in the ratio 1:1) or for non racemic mixtures in which one of the enantiomers is predominant, obtained by any physical or chemical method.

Below is shown by way of example the process for preparation of some of the compounds to which the present invention relates. These examples are shown for purposes of illustration only and should not be considered to limit the scope of the invention in any way.

EXAMPLE 1

Preparation of (−)-4-[5-(2,4-difluorophenyl)-4,5-dihydro-3-(trifluoromethyl)-1H-pyrazol-1-il]-benzenosulphonamide, (−)-8

Preparation of (±)-1-phenyl-5-(2,4-difluorophenyl)-4,5-dihydro-3-trifluoromethyl-1H-pyrazol, (±)-5

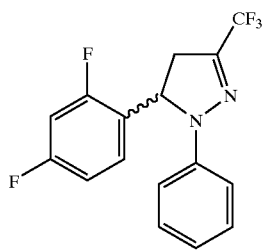

In a 50 mL beaker are introduced (E)-1,1,1-trifluoro-4-(2,4-difluorophenyl)-3-buten-2-one(2.66 g, 11.2 mmol), monohydrated p-toluensulphonic acid (2.1 g, 11.2 mmol) and phenylhydrazine chlorhydrate (1.33 g, 12.3 mmol) and heated to 110° C. A small amount of ethyl alcohol can be used to facilitate the initial mixture. After approximately 2 h (control by CCF) the mixture is allowed to cool and it is diluted with ethyl acetate. It is then washed with a saturated solution of $NaHCO_3$, dried with $MgSO_4$, filtered and the solvent evaporated at low pressure. The crude thus obtained (3.9 g) is recrystallised with methanol (2 mL) to precipitate 3.67 g (65%) of the pyrazoline (±)-5: pf=83–84° C.; IR (KBr) $\mu$ max (cm$^{-1}$) 1600, 1505, 1326; $^1$H-RMN (CDCl$_3$) δ (ppm): 7.28–6.72 (m, 8H), 5.64 (dd, J=13 Hz, J=7.5 Hz, 1H), 3.8–3.6 (m, 1H), 2.94 (dd, J=17.2 Hz, J=7 Hz, 1H).

Preparation of (±)-4-[5-(2,4-difluorophenyl)-4,5-dihydro-3-(trifluoromethyl)-1H-pyrazol-1-il]-sodium benzenosulphonate, (±)-6

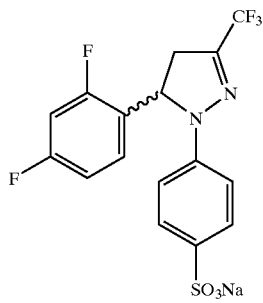

In a 100 mL beaker the pyrazoline (±)-5 (4.0 g, 12.27 mmol) is dissolved in dichloromethane (12 mL). The mixture is cooled at 0° C. and added on it drop by drop is chlorosulphonic acid (0.82 mL, 12.27 mmol). The stirring and temperature are maintained for 20 minutes, after which time the reaction mixture is slowly added on water (20 mL) at 4° C., stirring the assembly for 14 h at ambient temperature. The two phases are separated and the aqueous phase is washed with dichloromethane (5 mL). The aqueous phase is concentrated to two thirds of the initial volume and to this is added, under stirring, an aqueous solution of sodium hydroxide 1M (12.27 mL, 12.27 mmol). This precipitates a white solid which corresponds to sodium sulphonate (±)-6, which is filtered, washed with more water and dried (3.93 g, 75% yield): pf=292–295° C.; IR (KBr) $\mu$ max (cm$^{-1}$) 3430, 1600, 1570, 1425; $^1$H-RMN (CDCl$_3$/CD$_3$OD: 10/1) δ (ppm): 7.6 (d, J=8.8 Hz, 2H), 7.1–6.7 (m, 3H), 6.9 (d, J=8.8 Hz, 2H), 5.69 (dd, J=12.6 Hz, J=6.3 Hz, 1H).

Preparation of (−)-4-[5-(2,4-difluorophenyl)-4, 5-dihydro-3-(trifluoromethyl)-1-H-pyrazol-1-il]-benzenesulphonate de (+)-ephedrine, (−)-7·(+)-ephedrine.

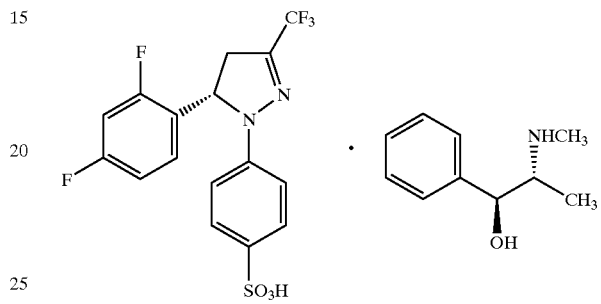

In a 2 L beaker are introduced sodium sulphonate (±)-6 (3.95 g, 9.23 mmol), (+)-ephedrine chlorhydrate (1.86 g, 9.23 mmol) and chloroform (79 mL). The mixture is shaken and heated to reflux for 10 minutes. It is allowed to cool slowly to ambient temperature, precipitating a solid (2.49 g) mixture of the salt (−)-7·(+)-ephedrine (enantiomeric excess above 98%) and sodium chloride formed in the process. This sample is used directly in the following reaction. If the sample is dissolved with a small amount of AcOEt, Washed with water, dried with MgSO$_4$ and the solvent is evaporated a pure fraction is obtained of the salt (−)-7·(+)-ephedrine: $[\alpha]_{20}^D$=−94.6 (c=2, MeOH); IR (KBr) $\mu$ max (cm$^{-1}$): 3410, 3040, 2860, 2780, 1595, 1570, 1500, 1420; $^1$H-RMN (CDCl$_3$/CD$_3$OD: 10/1) δ (ppm): 7.7 (d, J=9 Hz, 2H), 7.4–7.2 (m, 5H), 7.1–6.7 (m, 3H), 6.95 (d, J= 9 Hz, 2H), 5.65 (dd, J=12.5 Hz, J=6.5 Hz, 1H), 5.3 (d, J=2.2 Hz, 1H), 3.9–3.6 (m, 1H), 3.4–3.1 (m, 1H), 3.0 (dd, J=18.4 Hz, J=5.8 Hz, 1H), 2.76 (s, 3H), 1.9 (wide band, 1H), 1.0 (d, J=6 Hz, 3H).

Preparation of (−)-4-[5-(2,4-difluorophenyl)-4,5-dihydro-3-(trifluoromethyl)-1H-pyrazol-1-il]-sodium benzenesulphonate, (−)-6

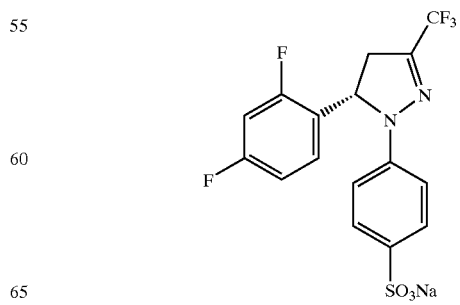

In a 50 mL beaker are introduced isopropyl alcohol (50 mL) and a mixture of the salt (−)-7·(+)-ephedrine (enantiomeric excess above 98%) and sodium chloride (2.49 g). The suspension obtained is shaken and sodium hydroxide 10 M (0.4 mL) is added on it. The solution is heated to reflux and 10 minutes later it is allowed to cool slowly to ambient temperature. A precipitate is obtained which once filtered, washed with isopropyl alcohol and dried corresponds to a mixture of sodium sulphonate (−)-6 and sodium chloride (1.86 g), which is directly used in the preparation of (−)-8. In order to determine the optical rotation of the compound (−)-6 it is possible to purify part of the sample by washing with water: $[\alpha]_{20}^{D}=-170.1$ (c=1, MeOH).

Preparation of (−)-4-[5-(2,4-difluorophenyl)-4,5-dihydro-3-(trifluoromethyl)-1H-pyrazol-1-il]-benzenosulphonamide, (−)-8

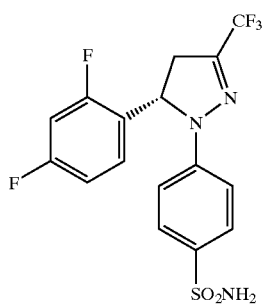

In a 1 L beaker is introduced a sample (72 g) mixture of sodium sulphonate (−)-6 (48.3 g, 112.8 mmol) and NaCl (23.7 g) on toluene (250 mL). The suspension is heated to 60° C., thionyl chloride is added (18 mL, 247.5 mmol), it is heated to reflux and left at this temperature for 2 hours at least. After the acid chloride formation reaction has finished the excess thionyl chloride is eliminated by its azeotropic distillation with toluene (190 mL; 76° C. at 60 mmHg). More toluene is added (190 mL) and it is again distilled in the same conditions.

For preparation of the sulphonamide the previous sample is diluted with toluene (190 mL), the mixture is cooled to 70° C., solid ammonium carbonate is added (22.6 g, 235 mmol), it is heated to 90° C. and shaken at this temperature for 2 h. When the reaction has finished (if necessary more ammonium carbonate is provided) water is added (300 mL) and it is maintained for 30 minutes at 90° C. the mixture is cooled to ambient temperature and an aqueous solution of 17.5% HCl is added until obtaining a pH of 6–7 and it is kept stirred for another 10 minutes. The precipitated solid is filtered, washed with toluene and dried to provide the sulphonamide (−)-8 (38.4 g, 84% yield). The product can be recrystallised with a mixture of isopropyl alcohol and water (60:40), giving an ee above 99%: pf=173–174° C.; $[\alpha]_{20}^{D}=-192.8$ (c=1, MeOH); IR (KBr) $\mu$ max (cm$^{-1}$): 3310, 3230, 1600, 1500, 1430; $^1$H-RMN (CDCl$_3$) δ (ppm): 7.76 (d, J=9 Hz, 2H), 7.04 (d, J=9 Hz, 2H), 7.1–6.75 (m, 3H), 5.71 (dd, J=12.4 Hz, J= 6.2 Hz, 1H), 4.74 (s, 2H), 3.9–3.7 (m, 1H), 3.03 (dd, J=19.8 Hz, J=6.2 Hz, 1H).

EXAMPLE 2

Preparation of (−)-1-(2,4-difluorophenyl)-4,5-dihydro-5-(4-methylsulphonylphenyl)-3-(trifluoromethyl)-1H-pyrazol, (−)-13

Preparation of (±)-1-(2,4-difluorophenyl)-4,5-dihydro-5-phenyl-3 -(trifluoromethyl)-1H-pyrazol, (±)-10

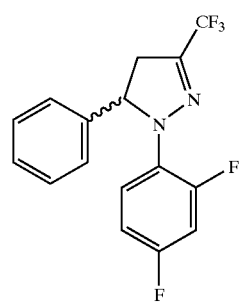

In a 50 mL beaker are introduced (E)-1,1,1-trifluoro-5-phenyl-3-buten-2-one (3.04 g, 15.2 mmol), monohydrated p-toluensulphonic acid (2.9 g, 15.2 mmol) and 2,4-difluorophenylhydrazine chlorhydrate (3.01 g, 16.7 mmol) and heated to 110° C. A small amount of ethyl alcohol can be used to facilitate the initial mixture. After approximately 2 hour (controlled by CCF) the mixture is allowed to cool and it is diluted with ethyl acetate. It is washed with a saturated solution of NaHCO$_3$, dried with MgSO$_4$, filtered and the solvent is evaporated at low pressure. The crude thus obtained is recrystallised with isopropyl alcohol (1 g/1 mL) precipitating 3.95 g (80%) of pyrazoline (O)-10: pf=52–54° C.; IR (KBr) $\mu$ max (cm$^{-1}$) 1598, 1511, 1414, 1324; $^1$H-RMN (CDCl$_3$) δ (ppm): 7.4–6.6 (m, 8H), 5.7–5.4 (m, 1H), 3.8–3.5 (m, 1H), 3.3–3.0 (m, 1H).

Preparation of (±)-4-[1-(2,4-difluorophenyl)-4,5-dihydro-3-(trifluoromethyl)-1H-pyrazol-5-il]-sodium benzenesulphonate, (±)-11

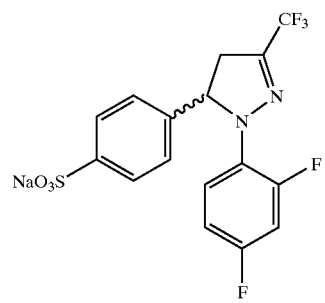

In a 100 mL beaker are dissolved pyrazoline (±)-10 (3.0 g, 9.2 mmol) in dichloromethane (1.5 mL). The mixture is cooled to 0° C. and onto it is added, drop by drop, chlorosulphonic acid (6.1 mL, 92 mmol). Coolant is coupled to it and the temperature is increased to 50° C. The shaking and temperature are maintained during 5 hours (controlled by CCF), the mixture is allowed to cool and diluted with dichloromethane (90 mL), at which time the reaction is slowly added on water (90 mL) at 4° C. the two phases are separated and two extractions are performed of the aqueous phase with dichloromethane (25 mL). The organic phase is dried with MgSO$_4$, filtered and the solvent evaporated at low pressure. The crude thus obtained (3.6 g) is introduced in a 25 mL beaker coupled to a coolant and on it is added water (13.4 mL). The suspension is heated to 70° C. and slowly added onto it, stirring, is an aqueous solution of sodium hydroxide 10M (1.7 mL, 17.04 mmol). The mixture is heated to reflux and is kept at this temperature for 10 minutes. It is allowed to cool slowly until reaching ambient temperature, precipitating a white solid that corresponds to sodium sulphonate (±)-11, which is filtered, washed with more water and dried (3.0 g, 82% yield): pf=271–273° C.; IR (KBr) $\mu$ max (cm$^{-1}$) 3477, 1617, 1513, 1416; $^1$H-RMN (CDCl$_3$) δ (ppm): 7.59 (d, J=8.5 Hz, 2H), 7.3–7.0 (m, 3H), 6.95 (d, J=8.5 Hz, 2H), 5.4 (m, 1H), 3.5 (m, 1H), 2.9 (m, 1H).

Preparation of (−)-4-[1-(2,4-difluorophenyl)-4,5-dihydro-3-(trifluoromethyl)-1H-pyrazol-5-yl]-benzenesulphonate of (+)-ephedrine, (−)-12·(+)-ephedrine

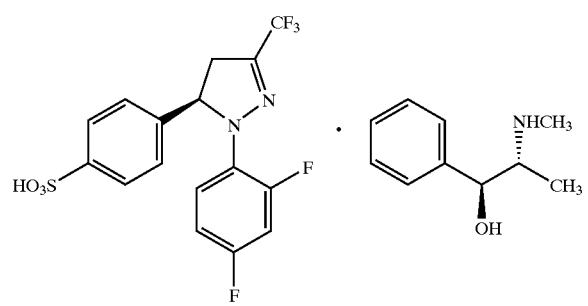

In a 50 mL beaker are introduced sodium sulphonate (±)-11 (2.45 g, 5.72 mmol), (+)-ephedrine chlorhydrate (1.15 g, 5.72 mmol) and toluene (24.5 mL). The mixture is shaken and heated to reflux for 10 minutes. It is allowed to cool slowly until reaching ambient temperature, precipitating a solid which is filtered and washed with more toluene. This provides 1.18 g, mixture of the salt (−)-12·(+)-ephedrine(enantiomeric excess of 84%) and of the sodium chloride formed in the process. This sample is directly used in the following reaction; IR (KBr) $\mu$ max (cm$^{-1}$) 3377, 3031, 1603, 1515, 1399; $^1$H-RMN (CDCl$_3$/CD$_3$OD: 10/1) δ (ppm): 7.76 (d, J=8 Hz, 2H), 7.4–7.2 (m, 6H), 7.19 (d, J=8 Hz, 2H), 6.75 (m, 2H), 5.6 (m, 1H), 5.35 (s, 1H), 3.65 (m, 1H), 3.3 (m, 1H), 3.15–3.0 (m, 1H), 2.76 (s, 3H), 2.65 (m, 2H), 1.07 (d, J=7 Hz, 3H).

Preparation of (−)-4-[1-(2,4-difluorophenyl)-4,5-dihydro-3-(trifluoromethyl)1-H-pyrazol-5-il]-sodium benzenesulphonate, (−)-11

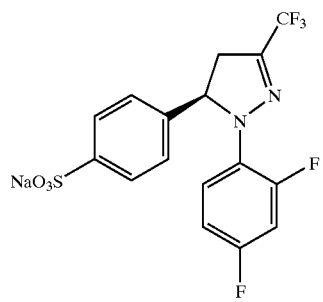

In a 10 mL beaker are introduced water (2.8 mL) and the mixture (1 g) of the salt (−)-7·(+)-ephedrine and sodium chloride (28% of total weight). The suspension obtained is shaken and added to it is sodium hydroxide 10M (0.3 mL). The solution is heated to reflux and 10 minutes later allowed to cool slowly to ambient temperature. A precipitate is obtained which once filtered, washed with water and dried corresponds to sodium sulphonate (−)-11 (0.34 g), which is used directly in preparation of the compound (−)-13: $[\alpha]_{20}^D$=−104.3 (c=1, MeOH).

Preparation of (−)-1-(2,4-difluorophenyl)-4,5-dihydro-5-(4-methylsulphonylphenyl)-3-(trifluoromethyl)-1H-pyrazol, (−)-13

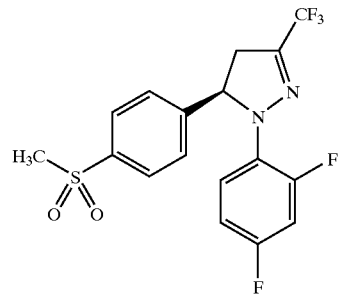

In a 10 mL beaker are dissolved the compound (−)-11 (230 mg, 0.54 mmol) in toluene (1.1 mL). The suspension is heated to 60° C., thionyl chloride is added (88 µL, 1.18 mmol), and it is kept at said temperature for at least 2 hours. At the end of the acid chloride formation reaction the excess thionyl chloride is eliminated by azeotropic distillation with toluene (76° C. at 60 mmHg). More toluene (1 mL) is added and again distilled in the same conditions. On the crude thus obtained are added water (1.15 mL), NaHCO$_3$ (95 mg, 1.13 mmol) and Na$_2$SO$_3$ (124 mg, 0.97 mmol), heating to 75° C. It is kept at this temperature for 2 hours and then allowed to cool to room temperature. The solvent is evaporated at low pressure and on the crude is added methyl alcohol (14 mL). After 1 hour at reflux it is filtered hot and the solvent evaporated at reduced pressure. The solid thus obtained (297 mg) is dissolved in methyl alcohol (2.8 mL) and onto this is added methyl iodide (44 µL, 0.7 mmol). This is heated to 55°

C. and kept at this temperature for 16 hours. The solvent is evaporated at low pressure, yielding 168 mg (77%) of crude. The product can be recrystallised with a mixture of toluene and cyclohexane: pf=86–9°; [$\alpha$]$20^D$=–86,1 (c=1, CH$_3$OH); IR (KBr) $\mu$ max (cm$^{-1}$): 1598, 1513, 1416; $^1$H-RMN (CDCl$_3$) $\delta$ (ppm): 7.87 (d, J=8.4 Hz, 2H), 7.5–7.2 (m, 3H), 6.9–6.6 (m, 2H), 5.7 (dd, J=6.5 Hz, J= 2.6 Hz, 1H), 3.8–3.6 (m, 1H), 3.2–2.9 (m, 1H), 3.02 (s, 3H).

What is claimed is:

1. A method of preparing a pyrazoline compound with the formula (±)-9

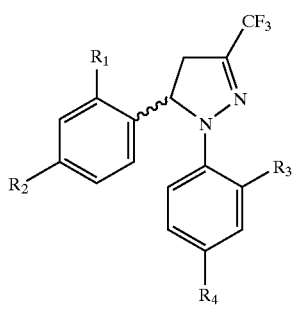

Formula 9 wherein
each of R$_1$ and R$_3$ which may be the same or different is selected from the group consisting of hydrogen, chlorine, fluorine, methyl, trifluoromethyl and methoxy; and
each of R$_2$ and R$_4$ which may be the same or different is selected from the group consisting of hydrogen, chlorine, fluorine, methyl, trifluoromethyl, methoxy, trifluoromethoxy, methylsulphonyl, aminosulphonyl and sodium sulphonate; and
with the condition that one of the substituents R$_2$ or R$_4$ is a sodium sulphonate group (SO$_3$Na); said method comprising:

(a) reacting a pyrazoline compound with the formula (±)-10

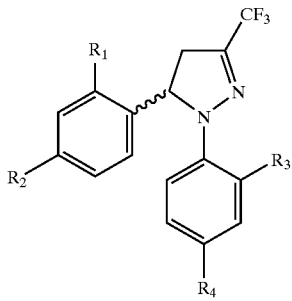

Formula 10 wherein
each of R$_1$ and R$_3$ which may be the same or different is selected from the group consisting of hydrogen, chlorine, fluorine, methyl, trifluoromethyl and methoxy; and
each of R$_2$ and R$_4$ which may be the same or different is selected from the group consisting of hydrogen, chlorine, fluorine, methyl, trifluoromethyl, methoxy, trifluoromethoxy, methylsulphonyl and aminosulphonyl;
with the condition that one of the substituents R$_2$ or R$_4$ represents an atom of hydrogen;
with chlorosulphonic acid, without a solvent or with a chlorinated solvent at temperatures between 0° C. and 100° C. to form an intermediate compound; and
(b) reacting said intermediate compound with sodium hydroxide resulting in the pyrazoline with the formula (±)-9.

* * * * *